United States Patent [19]

Bianchi et al.

[11] Patent Number: 4,594,443
[45] Date of Patent: Jun. 10, 1986

[54] DERIVATIVES OF 4-PHENYL-4-OXO-BUTEN-2-OIC ACID AND THERAPEUTIC USE THEREOF

[75] Inventors: Mario Bianchi; Fernando Barzaghi, both of Milan, Italy

[73] Assignee: Roussel-Uclaf, Paris, France

[21] Appl. No.: 642,249

[22] Filed: Aug. 20, 1984

[30] Foreign Application Priority Data

Aug. 25, 1983 [IT] Italy .................. 22648 A/83

[51] Int. Cl.$^4$ .......................... C07C 69/76
[52] U.S. Cl. .................. 560/053; 562/463; 562/464; 260/501.1; 514/545; 514/568
[58] Field of Search .............. 560/53; 562/463, 464; 260/501.1; 514/545, 568

[56] References Cited

U.S. PATENT DOCUMENTS

| | | | |
|---|---|---|---|
| 2,532,579 | 12/1950 | Thomas | 580/53 |
| 2,562,208 | 7/1951 | Papa et al. | 560/53 |
| 3,753,997 | 8/1973 | Ash et al. | 562/463 |
| 3,763,148 | 10/1973 | Ash et al. | 562/463 |
| 3,846,470 | 11/1974 | Raube et al. | 562/463 |
| 3,910,959 | 10/1975 | Vallet | 560/53 |
| 3,940,404 | 2/1976 | Ash et al. | 560/53 |
| 3,940,487 | 2/1976 | La Croix et al. | 560/53 |
| 3,953,463 | 4/1976 | Ash et al. | 560/53 |
| 4,017,517 | 4/1977 | Murata et al. | 560/53 |

FOREIGN PATENT DOCUMENTS

| | | | |
|---|---|---|---|
| 1282644 | 9/1962 | Fed. Rep. of Germany | 560/53 |
| 2047806 | 4/1972 | Fed. Rep. of Germany | 560/53 |
| 2103749 | 8/1972 | Fed. Rep. of Germany | 560/53 |
| 2501834 | 7/1975 | Fed. Rep. of Germany | 514/545 |
| 588108 | 6/1947 | United Kingdom | 560/53 |
| 1387733 | 3/1975 | United Kingdom | 560/53 |

OTHER PUBLICATIONS

*Journal of American Pharmaceutical Association*, vol. 37, No. 11, Nov. 1948, pp. 439-449.
*Chemical Abstracts*, vol. 88, No. 5, Jan. 30, 1978, abstract 37442p.
*Journal of the American Chemical Society*, vol. 71, No. 4, Apr. 1949, F. K. Kirchner et al, pp. 1210-1213.
*Journal of the American Chemical Society*, vol. 70, No. 10, Oct. 1948, D. papa et al, pp. 3356-3360.
*European Journal of Medical Chemistry Chimica Therapeutica*, vol. 12, Jan.-Feb. 1977, pp. 17-20.
*European Journal of Medical Chemistry Chimica Therapeutica*, vol. 13, No. 3, May-Jun. 1978, H. Orzalesi et al, pp. 259-264.

*Primary Examiner*—Paul J. Killos
*Attorney, Agent, or Firm*—Stevens, Davis, Miller & Mosher

[57] ABSTRACT

Compounds of the formula (I):

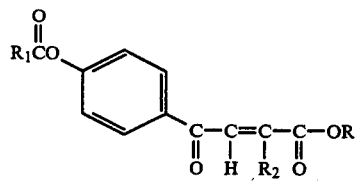

in which $R_1$ represents alkyl containing from 1 to 18 carbon atoms, $R_2$ represents hydrogen or alkyl containing from 1 to 8 carbon atoms and R represents hydrogen or alkyl containing from 1 to 8 carbon atoms, as well as the alkali metal, alkaline-earth metal or amine salts thereof, in which R represents hydrogen. Also, method of preparing same, compositions containing same and therapeutic treatment therewith.

24 Claims, No Drawings

DERIVATIVES OF 4-PHENYL-4-OXO-BUTEN-2-OIC ACID AND THERAPEUTIC USE THEREOF

The present invention relates to derivatives of 4-phenyl-4-oxo-buten-2-oic acid, the process for preparing them, their therapeutic application and the compositions containing them.

More particularly, this invention relates to compounds of the formula (I):

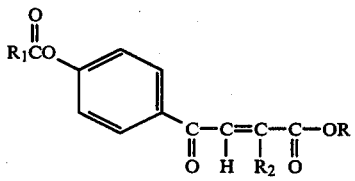

in which $R_1$ represents alkyl containing from 1 to 18 carbon atoms, $R_2$ represents hydrogen or alkyl containing from 1 to 8 carbon atoms and R represents hydrogen or alkyl containing from 1 to 8 carbon atoms, as well as the alkali metal, alkaline-earth metal or amine salts of said compounds, in which R represents a hydrogen atom.

Among the preferred values for $R_1$ are alkyl containing from 1 to 6 carbon atoms and particularly methyl, ethyl, n-propyl and n-butyl.

When $R_2$ represents alkyl, it is preferred to be methyl.

When R represents alkyl, it is preferred to contain from 1 to 5 carbon atoms, for example, methyl, ethyl, n-propyl, isopropyl, n-butyl, isobutyl, tert-butyl or n-pentyl.

The alkali or alkaline-earth metal salts of the compounds of the formula (I) in which R represents hydrogen are preferably the salts of sodium, potassium, lithium or calcium.

The amine salts of the above compound, in which R represents a hydrogen atom, are the usual amine salts. Among the usual amine salts, there can be mentioned the monoalkylamines, such as, for example, methylamine, ethylamine and propylamine, the dialkylamines, such as, for example, dimethylamine, diethylamine and di-n-propylamine and the trialkylamines, such as triethylamine. There can also be mentioned piperidine, morpholine, piperazine or pyrrolidine.

The compounds of formula (I) can exist in the E or Z isomeric form (trans or cis).

Particularly preferred among the compounds of formula (I) are those in which R represents hydrogen, as well as their alkali metal, alkaline-earth metal or amine salts, and particularly those in which $R_2$ represents a hydrogen atom.

Quite particularly preferred are the compounds of the formula (I), in which $R_1$ represents methyl or ethyl.

The compounds of the above formula (I) in the different possible isomeric forms, as well as the alkali metal, alkaline-earth metal or amine salts thereof, in which R represents hydrogen, display useful pharmacological properties; notably, they exhibit an important anti-ulcerous activity.

In addition, when put in contact with the gastric mucosa, they exhibit an anti-gastric-secretion and cyto-protecting activity.

All of the compounds of formula (I) constitute, according to the invention, medicaments which are very useful in human medicine, notably for the treatment of hyperchlorhydrias, gastric and gastro-duodenal ulcers, gastrities, hiatal hernias, and gastric and gastro-duodenal disorders accompanied by gastric hyperacidity.

The posology, variable according to the compound employed and the disorder to be treated, can vary, for example, between 0.05 g and 2 g per day by oral route in an adult.

The present invention also has as its object the pharmaceutical compositions which contain, as active principle, at least one of the previously-mentioned compounds. These compositions are produced in such a way as to enable them to be administered by digestive or parenteral route.

They can be solid or liquid, and are prepared in the pharmaceutical forms currently used in human medicine, such as, for example, plain or sugar-coated tablets, capsules, granules, suppositories and injectable preparations; they are prepared according to the usual methods.

The active principle or principles can be incorporated with the excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, and the various wetting, dispersing or emulsifying agents and preservatives.

The invention also has as its subject a process for the preparation of the compounds of formula (I), as well as their salts, characterized in that a compound with the formula (II):

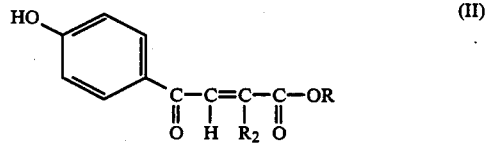

in which R and $R_2$ are defined as previously, is subjected to the action of an acid $R_1CO_2H$ or of a functional derivative of this acid, so as to obtain the corresponding compound with the formula (I) which, if desired, is salified or esterified.

As functional derivative of the acid, it is preferential to use a halide of the acid, for example, a chloride or an anhydride of the acid.

The alkali metal, alkaline-earth metal or amine salts of the compounds of formula (I) can be prepared by a usual process, such as, for example, by the action on the said compounds of the corresponding bases or by a double decomposition reaction, or by any conventional process known for this type of ethylene carboxylic acids.

The salification reaction is preferably conducted in a solvent or a mixture of solvents, such as water, ethyl ether, acetone, ethyl acetate, tetrahydrofuran or dioxan.

The compounds of formula (I), in which R represents alkyl containing from 1 to 8 carbon atoms, can be prepared either by starting with compounds with the formula (II), in which R represents alkyl, or by starting with compounds with the formula (I) in which R represents a hydrogen atom, in the usual way by the action of an alcohol with the formula ROH, preferably in an acid medium. The acid can, for example, be hydrochloric acid, phosphoric acid or paratoluene sulphonic acid.

The compounds with the formula (II) used as starting compounds are known products which can, for example, be prepared according to the method described in the published U.K. patent application No. 2,108,385.

The following examples illustrate the invention without, however, limiting it.

EXAMPLE 1

(E) 4-(4-acetoxyphenyl)-4-oxo-buten-2-oic acid

A solution of 6 g of (E) 4-(4-hydroxyphenyl)-4-oxo-buten-2-oic acid (described in J.A.C.S. 70, 3356, 1948) in 50 cm³ of acetic anhydride is heated for 1½ hours at 50° C. It is then cooled to ambient temperature, diluted with water, concentrated, and then extracted with ethyl acetate. The organic phase is separated, dried, and the solvent is evaporated. The residue is recrystallized from ethanol at 70%, and 4.5 g of the expected product is obtained. m.p. 154°–156° C.

Analysis-$C_{12}H_{10}O_5$: Calculated: C% 61.54, H% 4.30. Found: C% 61.48, H% 4.18.

EXAMPLE 2

(E) 4-(4-propanoyloxyphenyl)-4-oxo-buten-2-oic acid

A mixture of 2.5 g of (E) 4-(4-hydroxyphenyl)-4-oxo-buten-2-oic acid and 25 cm³ of propanoic anhydride is heated to 100° C. for 2 hours. The excess anhydride is evaporated, the residue is taken up with benzene and evaporated to dryness. The residue is chromatographed on silica, eluting with a mixture of benzene, ethyl acetate and acetic acid (50-50-1). The product is crystallized from water and, after drying, 1.9 g of the expected product is obtained. m.p. 140°–142° C.

Analysis-$C_{13}H_{12}O_5$: Calculated: C% 62.90, H% 4.87. Found: C% 62.96, H% 4.77.

PHARMACEUTICAL FORMS

EXAMPLE 3

Tablets

Tablets were prepared according to the following formula:
Product of Example 1: 100 mg
Excipient q.s. for a tablet finished at: 300 mg
(Detail of the excipient: lactose, wheat starch, treated starch, rice starch, magnesium stearate, talc)

EXAMPLE 4

Capsules

Capsules were prepared according to the following formula:
Product of Example 2: 100 mg
Excipient q.s. for a capsule finished at: 300 mg
(Detail of excipient: talc, magnesium stearate, aerosil)

PHARMACOLOGICAL STUDY

A. Toxicity

The lethal dose 50 ($LD_{50}$) was evaluated after administration of the products by oral route to mice.
The following results were obtained:
Products of Example 1: $LD_{50}$=350 mg/kg
Product of Example 2: $LD_{50}$=750 mg/kg

B. Determination of Anti-Gastric-Secretion Activity

The technique utilized is described by H. Shay et al in *Gastroenterology* 5, 43 (1945).

Male rats weighing about 200 g are used which have been without food for 48 hours, but have had available as much as they wanted of 8% glucose solution. After lightly anaesthetizing the rats with ether, their pylorus was ligatured, then, at the end of the operation, the product under test at various doses, or for the control animals, a solution of carboxymethyl cellulose at 0.5% is administered by intra-duodenal route; the abdominal incision is then sutured.

Three hours later the animals were killed and their stomachs were removed after ligature of the oesophagus. The gastric juice was removed and centrifuged. The volume is then measured and, for 100 μl of gastric juice, the total acidity is determined by titrating to pH 7 with 0.01N sodium hydroxide.

The percentages of variation of total acidity of the gastric secretions were calculated in relation to the results obtained with the control animals.

The results were the following for a dose of 10 mg/kg:
Product of Example 1: −77%
Product of Example 2: −73%

What is claimed is:

1. Compounds of the formula (I)

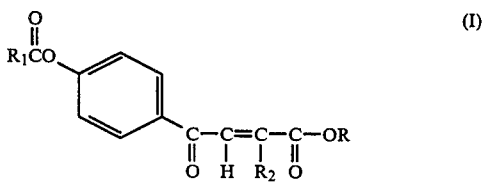

in which $R_1$ represents alkyl containing from 1 to 18 carbon atoms, $R_2$ represents hydrogen or alkyl containing from 1 to 8 carbon atoms and R represents hydrogen or alkyl containing from 1 to 8 carbon atoms, as well as the alkali metal, alkaline-earth metal or amine salts thereof, in which R represents hydrogen.

2. Compounds of the formula (I) as defined in claim 1, in which R represents hydrogen.

3. Compounds of the formula (I) as defined in claim 1, in which $R_2$ represents a hydrogen atom.

4. Compounds of the formula (I) as defined in claim 2, in which $R_2$ represents a hydrogen atom.

5. Compounds of the formula (I) as defined in claim 1, in which $R_1$ repressents methyl or ethyl.

6. Compounds of the formula (I) as defined in claim 2, in which $R_1$ repressents methyl or ethyl.

7. Compounds of the formula (I) as defined in claim 3, in which $R_1$ repressents methyl or ethyl.

8. Compounds as defined in claim 1, selected from the group consisting of (E)4-(4-acetoxyphenyl)-4-oxo-buten-2-oic acid and (E)4-(4-propanoyloxyphenyl)-4-oxo-buten-2-oic acid, as well as their alkali metal, alkaline-earth metal or amine salts.

9. A pharmaceutical composition for treatment of hyperchlorhydria, gastric or gastro-duodenal ulcers, gastritis, hiatal herias, or gastric or gastro-duodenal ailments accompanied by gastric hyperacidity, comprising:
   a therapeutically effective amount of a compound of formula (I) as claimed in claim 1; and
   a pharmaceutically acceptable excipient.

10. A pharmaceutical composition for treatment of hyperchlorhydria, gastric or gastro-duodenal ulcers, gastritis, hiatal hernias, or gastric or gastro-duodenal ailments accompanied by gastric hyperacidity, comprising:

a therapeutically effective amount of a compound of formula (I) as claimed in claim 2; and
a pharmaceutically acceptable excipient.

11. A pharmaceutical composition for treatment of hyperchlorhydria, gastric or gastro-duodenal ulcers, gastritis, hiatal hernias, or gastric or gastro-duodenal ailments accompanied by gastric hyperacidity, comprising:
a therapeutically effective amount of a compound of formula (I) as claimed in claim 3; and
a pharmaceutically acceptable excipient.

12. A pharmaceutical composition for treatment of hyperchlorhydria, gastric or gastro-duodenal ulcers, gastritis, hiatal hernias, or gastric or gastro-duodenal ailments accompanied by gastric hyperacidity, comprising:
a therapeutically effective amount of a compound of formula (I) as claimed in claim 4; and
a pharmaceutically acceptable excipient.

13. A pharmaceutical composition for treatment of hyperchlorhydria, gastric or gastro-duodenal ulcers, gastritis, hiatal hernias, or gastric or gastro-duodenal ailments accompanied by gastric hyperacidity, comprising:
a therapeutically effective amount of a compound of formula (I) as claimed in claim 5; and
a pharmaceutically acceptable excipient.

14. A pharmaceutical composition for treatment of hyperchlorhydria, gastric or gastro-duodenal ulcers, gastritis, hiatal hernias, or gastric or gastro-duodenal ailments accompanied by gastric hyperacidity, comprising:
a therapeutically effective amount of a compound of formula (I) as claimed in claim 6; and
a pharmaceutically acceptable excipient.

15. A pharmaceutical composition for treatment of hyperchlorhydria, gastric or gastro-duodenal ulcers, gastritis, hiatal hernias, or gastric or gastro-duodenal ailments accompanied by gastric hyperacidity, comprising:
a therapeutically effective amount of a compound of formula (I) as claimed in claim 7; and
a pharmaceutically acceptable excipient.

16. A pharmaceutical composition for treatment of hyperchlorhydria, gastric or gastro-duodenal ulcers, gastritis, hiatal hernias, or gastric or gastro-duodenal ailments accompanied by gastric hyperacidity, comprising:
a therapeutically effective amount of a compound of formula (I) as claimed in claim 8; and
a pharmaceutically acceptable excipient.

17. A method for treating a patient suffering from hyperchlorhydria, gastric or gastro-duodenal ulcers, gastritis, hiatal hernias, or gastric or gastro-duodenal ailments accompanied by gastric hyperacidity, comprising administering to said patient a therapeutically effective amount of a compound as defined in claim 1.

18. A method for treating a patient suffering from hyperchlorhydria, gastric or gastro-duodenal ulcers, gastritis, hiatal hernias, or gastric or gastro-duodenal ailments accompanied by gastric hyperacidity, comprising administering to said patient a therapeutically effective amount of a compound as defined in claim 2.

19. A method for treating a patient suffering from hyperchlorhydria, gastric or gastro-duodenal ulcers, gastritis, hiatal hernias, or gastric or gastro-duodenal ailments accompanied by gastric hyperacidity, comprising administering to said patient a therapeutically effective amount of a compound as defined in claim 3.

20. A method for treating a patient suffering from hyperchlorhydria, gastric or gastro-duodenal ulcers, gastritis, hiatal hernias, or gastric or gastro-duodenal ailments accompanied by gastric hyperacidity, comprising administering to said patient a therapeutically effective amount of a compound as defined in claim 4.

21. A method for treating a patient suffering from hyperchlorhydria, gastric or gastro-duodenal ulcers, gastritis, hiatal hernias, or gastric or gastro-duodenal ailments accompanied by gastric hyperacidity, comprising administering to said patient a therapeutically effective amount of a compound as defined in claim 5.

22. A method for treating a patient suffering from hyperchlorhydria, gastric or gastro-duodenal ulcers, gastritis, hiatal hernias, or gastric or gastro-duodenal ailments accompanied by gastric hyperacidity, comprising administering to said patient a therapeutically effective amount of a compound as defined in claim 6.

23. A method for treating a patient suffering from hyperchlorhydria, gastric or gastro-duodenal ulcers, gastritis, hiatal hernias, or gastric or gastro-duodenal ailments accompanied by gastric hyperacidity, comprising administering to said patient a therapeutically effective amount of a compound as defined in claim 7.

24. A method for treating a patient suffering from hyperchlorhydria, gastric or gastro-duodenal ulcers, gastritis, hiatal hernias, or gastric or gastro-duodenal ailments accompanied by gastric hyperacidity, comprising administering to said patient a therapeutically effective amount of a compound as defined in claim 8.

* * * * *